(12) United States Patent
Carrasco Niño

(10) Patent No.: US 11,191,795 B2
(45) Date of Patent: Dec. 7, 2021

(54) HERBAL COMPOSITIONS AND METHODS FOR TREATING HERPES

(71) Applicant: Beatriz Eugenia Carrasco Niño, San Diego, CA (US)

(72) Inventor: Beatriz Eugenia Carrasco Niño, San Diego, CA (US)

( * ) Notice: Subject to any disclaimer, the term of this patent is extended or adjusted under 35 U.S.C. 154(b) by 83 days.

(21) Appl. No.: 16/280,724

(22) Filed: Feb. 20, 2019

(65) Prior Publication Data

US 2020/0261522 A1 Aug. 20, 2020

(51) Int. Cl.

| A61K 36/185 | (2006.01) |
| A61K 9/00 | (2006.01) |
| A61P 31/22 | (2006.01) |
| A61K 36/28 | (2006.01) |
| A61K 9/06 | (2006.01) |

(52) U.S. Cl.
CPC .......... *A61K 36/185* (2013.01); *A61K 9/0014* (2013.01); *A61K 9/06* (2013.01); *A61K 36/28* (2013.01); *A61P 31/22* (2018.01)

(58) Field of Classification Search
None
See application file for complete search history.

(56) References Cited

U.S. PATENT DOCUMENTS

| 4,478,853 A | 10/1984 | Chaussee |
| 5,639,460 A | 6/1997 | Raymond |
| 5,858,232 A | 1/1999 | Meissner |
| 7,858,126 B2 | 12/2010 | Singh et al. |
| 8,846,114 B1 * | 9/2014 | Makela ................. A61K 36/38 424/725 |

FOREIGN PATENT DOCUMENTS

EP   0 522 624 A1   1/1993

OTHER PUBLICATIONS

Rojas et al., Screening for antimicrobial activity of ten medicinal plants used in Colombian folkloric medicine: A possible alternative in the treatment of non-nosocomial infections, 2006, BMC Complementary and Alternative Medicine, 6:2, pp. 1-6.*
Mostafa et al. The Genus *Jacaranda* (Bignoniaceae): An Updated Review, 2014, Pharmacognosy Communications, 4:3, pp. 31-39.*
Chisaca, Formula, Herpes Simple y Zoster, Antiviral medication, 1 page.
Hardenia et al., "Emulgel: An Emergent Tool in Topical Drug Delivery," IJPSR, 2014, vol. 5, Issue 5, pp. 1653-1660.

* cited by examiner

*Primary Examiner* — Terry A McKelvey
*Assistant Examiner* — Catheryne Chen
(74) *Attorney, Agent, or Firm* — Squire Patton Boggs (US) LLP

(57) ABSTRACT

The present invention provides herbal formulations, methods for their preparation, and methods of treating herpes simplex. The formulations can provide good permeability and bioavailability at the target site.

20 Claims, No Drawings

HERBAL COMPOSITIONS AND METHODS FOR TREATING HERPES

BACKGROUND OF THE INVENTION

Infection with herpes simplex virus (HSV), the pathogen that causes cold sores (generally HSV-1) and genital herpes (generally HSV-2), is a contagious virus that infects around 70% of the population. It lies dormant in the sensory nerve ganglia until it is reactivated by a trigger. Triggers for active infection include fatigue, stress, another viral infection, fever, dental procedures, hormone fluctuations, and extensive sun exposure. When active, the virus produces painful lesions at or near the site of infection, and it can infect other body sites or other people by contact. Active herpes usually begins with a tingling or burning sensation at the site of attack, followed by inflammation and papule formation, then painful vesicles that break open and form a sore. The sore gradually dries, scabs over, and heals, typically requiring 10 to 15 days.

Herpes can be treated with antiviral drugs, such as acyclovir, valacyclovir, and ganciclovir. These drugs typically reduce the time necessary for lesion formation and healing, but they can have side effects, such as depression, nausea, pain, and in rare cases, renal toxicity. Non-prescription remedies, such as lidocaine or menthol, are milder alternatives that treat the inflammation and pain of herpes lesions, but may not shorten the time required for lesion healing.

In light of the foregoing, there is a need for safe and effective alternative treatments for herpes. The present invention satisfies these and other needs.

BRIEF SUMMARY OF THE INVENTION

The present invention relates generally to herbal compositions of use in treating herpes and methods of treating herpes.

In some aspects, the invention provides an herbal composition, wherein the composition comprises:
- a first plant matter or preparation thereof, wherein the first plant matter is from *Jacaranda* sp.; and
- a second plant matter or preparation thereof, wherein the second plant matter is from *Spilanthes* sp.

In some embodiments, the invention provides an herbal composition that further comprises one or more agents selected from the group consisting of a moisturizing agent, a thickening agent, a pH-adjusting agent, and a preservative.

In some aspects, the invention provides method for the topical treatment of herpes, wherein the method comprises administering the herbal composition disclosed herein to a patient.

These and other objects, aspects, and embodiments will become more apparent when read with the following detailed description.

DETAILED DESCRIPTION OF THE INVENTION

I. Definitions of Terms

The terms "a," "an," or "the" as used herein not only includes aspects with one member, but also includes aspects with more than one member. For example, an embodiment including "a thickening agent and a preservative" should be understood to present some embodiments with an additional thickening agent or agents, an additional preservative or preservatives, or both.

The term "about" as used herein to modify a numerical value indicates a defined range around that value. If "X" were the value, "about X" would generally indicate a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

When "about" is applied to the beginning of a numerical range, it applies to both ends of the range. Thus, "from about 5% to 20%" is equivalent to "from about 5% to about 20%." When "about" is applied to the first value of a set of values, it applies to all values in that set. Thus, "about 7, 9, or 11%" is equivalent to "about 7%, about 9%, or about 11%."

"Agent" as used herein indicates a compound or mixture of compounds that, when added to a composition, tend to produce a particular effect on the composition's properties. For example, a composition comprising a thickening agent is likely to be more viscous than an otherwise identical comparative composition that lacks the thickening agent.

"Formulation," "herbal composition," and "composition" as used interchangeably herein are equivalent terms referring to a herbal composition of matter, which preferably is useful for the treatment of herpes (e.g., fever blisters caused by herpes type I or type II).

"Monohydric alcohol" as used herein includes straight- or branched-chain alkyl alcohols with a single hydroxyl group. Representative monohydric alcohols include methanol, ethanol, n-propanol, isopropanol, n-butanol, t-butanol, n-pentanol, 3-pentanol, 2-methoxyethanol, 2-(2-ethoxyethoxy)ethanol, oleyl alcohol, and the like.

The term "or" as used herein should in general be construed non-exclusively (i.e., "or" is a disjunctive "or"). For example, an embodiment of "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

The term "pH adjusting agent" as used herein refers to a compound added to the compositions of the present application for the purpose of changing the pH of the composition. Examples of such agents include pharmaceutically acceptable acids, pharmaceutically acceptable bases, and pharmaceutically acceptable buffers.

The term "pharmaceutically acceptable" means compatible with the treatment of animals, and in particular, humans.

The term "pharmaceutically acceptable salt" means a pharmaceutically acceptable acid addition salt or a pharmaceutically acceptable basic addition salt. The formation of a desired compound salt is achieved using standard techniques. For example, the neutral compound is treated with an acid or base in a suitable solvent and the formed salt is isolated by filtration, extraction, or any other suitable method.

"Surfactant" as used herein includes a surface-active agent. Surfactants reduce the surface tension of a solvent in which they are dissolved.

"Thickening agent" as used herein includes an agent or combination of agents that increases the viscosity of a composition. A thickening agent may be a pure substance, or it may comprise, consist essentially of, or consist of a mixture of different chemical entities. Exemplary thickening agents include cellulose polymers, carbomer polymers, carbomer derivatives, cellulose derivatives, polyvinyl alcohol, poloxamers, polysaccharides, and the like, as well as mixtures thereof.

"Topical formulation" as used herein includes a composition that is suitable for topical application to the skin, lips, or a mucosa. Preferably, the topical formulation may, for example, be used to confer a therapeutic or cosmetic benefit to its user.

The term "treating" or "treatment" as used herein (and as well understood in the art) means an approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable.

"Treating" and "treatment" as used herein also include prophylactic treatment. Treatment methods comprise administering to a subject a therapeutically effective amount of an active composition. The administering step may consist of a single administration, but preferably will include a series of administrations. The length of the treatment period depends on a variety of factors, such as the severity of the condition, the past history of the subject, the immunity or resistance of the person, any genetic predisposition to attacks, the nutrition of the person, the person's other illnesses or general health, the concentration and activity of the composition used in the treatment, and the like. It will also be appreciated that the effective dosage of a composition used for the treatment or prophylaxis may increase or decrease over the course of a particular treatment or prophylaxis regime. Changes in dosage may result. In some instances, chronic administration may be required. For example, the compositions are administered to the subject in an amount and for a duration sufficient to treat the patient.

The term "w/w" or "wt/wt" means a percentage by weight, which is expressed as 100 multiplied by the ratio of the weight of the ingredient or agent to the total weight of the composition. As a default unless indicated otherwise, the percentages disclosed herein are w/w.

II. Compositions

In some embodiments, the invention provides an herbal composition, wherein the composition comprises:
a first plant matter or preparation thereof, wherein the first plant matter is from *Jacaranda* sp.; and
a second plant matter or preparation thereof, wherein the second plant matter is from *Spilanthes* sp.
In some embodiments, the herbal composition comprises one, two, three, or four agents selected from the group consisting of:
(i) a moisturizing agent;
(ii) a thickening agent;
(iii) a pH-adjusting agent; and
(iv) a preservative.

A. First Plant Matter

In some embodiments, the invention provides an herbal composition, wherein the composition comprises a first plant matter or preparation thereof, wherein the first plant matter is from *Jacaranda* sp.

In some embodiments, the *Jacaranda* is sect. *Dilobos*. In some embodiments, the *Jacaranda* sp. is *Jacaranda caroba*. In some embodiments, the *Jacaranda* sp. is *Jacaranda oxyphylia*, Chamisso.

In some embodiments, the *Jacaranda* sp. is sect. *Monolobos*. In some embodiments, the *Jacaranda* sp. is *Jacaranda caerulea*. In some embodiments, the *Jacaranda* sp. is *Jacaranda caucana*, Pittier. In some embodiments, the *Jacaranda* sp. is *Jacaranda decurrens*. In some embodiments, the *Jacaranda* sp. is *Jacaranda mimosifolia.*

In some embodiments, the first plant matter or preparation thereof is a leaf, a stem, a bark, a flower, a fruit, a seed, or a root. In some embodiments, the first plant matter or preparation thereof is a leaf, a stem, a bark, a flower, a fruit, or a seed. In some preferred embodiments, the first plant matter or preparation thereof is a leaf.

In some embodiments, the first plant matter or preparation thereof is fresh plant material, dried plant material, a powder, a paste, an extract, an infusion, a decoction, or an essential oil. In some embodiments, the first plant matter or preparation thereof is fresh plant material or dried plant material. In some embodiments, the first plant matter or preparation thereof is a powder, a paste, a juice, an extract, an infusion, a decotion, or an essential oil. In some embodiments, the first plant matter or preparation thereof is a decotion. In some embodiments, the first plant matter or preparation thereof is an extract. In some embodiments, the first plant matter or preparation thereof is a decotion. In some embodiments, the first plant matter or preparation thereof is a powder or a paste. In some embodiments, the first plant matter or preparation thereof is a powder. In some embodiments, the second plant matter or preparation thereof is an extract or a tincture.

In some embodiments, the first plant matter or preparation thereof is included at a concentration between about 1 and 25% w/w of the formulation (e.g., about 1.0, 1.25, 1.5, 1.75, 2.0, 2.25, 2.5, 2.75, 3.0, 3.5, 4.0, 4.5, 5.0, 5.5, 6, 6.5, 7, 7.5, 8, 8.5, 9, 9.5, 10, 11, 12, 12.5, 13, 14, 15, 16, 17, 18, 19, 20, 21, 22, 23, 24, or 25). In some embodiments, the first plant matter or preparation thereof is included at a concentration between about 5% and 40% w/w (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40). In some embodiments, the first plant matter or preparation thereof is included at between about 1% and 10% w/w (e.g., about 1.0, 1.25, 1.5, 1.75, 2.0, 2.25, 2.5, 2.75, 3.0, 3.5, 4.0, 4.5, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, or 10.075, 2.0, 2.25, 2.5, 2.75, 3.0, 3.5, 4.0, 4.5, 5.0, 0.5.5, 6.0, 6.5, 7.0, 7.5, 8.0, 8.5, 9.0, 9.5, or 10.0).

B. Second Plant Matter

In some embodiments, the invention provides an herbal composition, wherein the composition comprises a second plant matter or preparation thereof, wherein the second plant matter is from *Spilanthes* sp.

In some embodiments, the *Spilanthes* sp. is *Spilanthes americana.*

In some embodiments, the first plant matter or preparation thereof is a leaf, a stem, a bark, a flower, a seed, or a root. In some embodiments, the second plant matter or preparation thereof is a leaf, a stem, a bark, a flower, or a seed. In some embodiments, the second plant matter or preparation thereof is a leaf, a stem, a flower, or a seed. In some embodiments, the second plant matter or preparation thereof is a leaf.

In some embodiments, the second plant matter or preparation thereof is fresh plant material, dried plant material, a powder, a paste, a tincture, an extract, an infusion, a decoction, or an essential oil. In some embodiments, the second plant matter or preparation thereof is fresh plant material or dried plant material. In some embodiments, the second plant matter or preparation thereof is a powder, a paste, a juice, a tincture, an extract, an infusion, a decoction, or an essential oil. In some embodiments, the second plant matter or preparation thereof is a powder or a paste. In some embodiments, the second plant matter or preparation thereof is a powder. In some embodiments, the second plant matter or preparation thereof is an extract or a tincture.

In some embodiments, the second plant matter or preparation thereof is included at a concentration between about 1 and 20% w/w of the formulation (e.g., about 1.0, 1.25, 1.5, 1.75, 2.0, 2.25, 2.5, 2.75, 3.0, 3.5, 4.0, 4.5, 5.0, 5.5, 6, 6.5, 7, 7.5, 8, 8.5, 9, 9.5, 10, 11, 12, 12.5, 13, 14, 15, 16, 17, 18, 19, or 20). In some embodiments, the second plant matter or preparation thereof is included at a concentration between about 5% and 40% w/w (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40). In some embodiments, the second plant matter or preparation thereof is included at between about 1% and 5% w/w (e.g., about 1.0, 1.25, 1.5, 1.75, 2.0, 2.25, 2.5, 2.75, 3.0, 3.5, 4.0, 4.5, or 5.0).

C. Moisturizing Agents

In some embodiments, the compositions of the present invention comprise moisturizing agents so that the formulations can maintain or increase the moisture content of the skin to which the composition is applied (e.g., the lips or area around the lips). Moisturizing agents may be added to the formulations in addition to the components otherwise described, which in some embodiments may also aid in maintaining or improving the skin condition of the user.

In some embodiments, the moisturizing agent is included at a concentration between about 0.1 and 20% w/w (e.g., about 0.1, 0.2, 0.3, 0.4, 0.5, 0.6, 0.7, 0.8, 0.9, 1.0, 1.25, 1.5, 1.75, 2.0, 2.25, 2.5, 2.75, 3.0, 3.5, 4.0, 4.5, 5.0, 5.5, 6, 6.5, 7, 7.5, 8, 8.5, 9, 9.5, 10, 11, 12, 12.5, 13, 14, 15, 16, 17, 18, 19, or 20). In some embodiments, the moisturizing agent is included at a concentration between about 0.5% and 10% w/w (e.g., about 0.5, 0.6, 0.7, 0.8, 0.9, 1.0, 1.25, 1.5, 1.75, 2.0, 2.25, 2.5, 2.75, 3.0, 3.5, 4.0, 4.5, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, or 10.0). In some embodiments, the moisturizing agent is included at between about 1% and 5% w/w (e.g., about 1.0, 1.25, 1.5, 1.75, 2.0, 2.25, 2.5, 2.75, 3.0, 3.5, 4.0, 4.5, or 5.0).

Moisturizing agents are generally separated into two broad classes based on their function. The first class of moisturizing agents functions by forming an occlusive barrier to prevent water evaporation from the stratum corneum. The second class of moisturizing agents penetrate into the stratum corneum and physically bind water to prevent evaporation. The first class of moisturizing agents is subdivided into compounds which are waxes at room temperature and compounds which are liquid oils. The second class of moisturizing agents includes those which are water soluble and are often referred to as humectants.

Suitable moisturizing agents may be selected from any of the classes known in the art. A general list of useful moisturizing agents appears, for example, in U.S. Pat. No. 4,478,853 and in EP patent application 0 522 624A1 as well as in the CTFA Cosmetic Ingredient Handbook published by The Cosmetic, Toiletry, and Fragrance Association, Wash. D.C. (1992) under the listings "Skin Conditioning agents," "emollients," "humectants," "miscellaneous" and "occlusive."

In some aspects, moisturizing agents may be chosen from the following non-limiting list of general moisturizing agents, occlusive moisturizing agents, and humectants.

Examples of general moisturizing agents include short-chain alkyl or aryl esters ($C_1$-$C_7$) of long-chain straight- or branched-chain alkyl or alkenyl alcohols or acids ($C_8$-$C_{32}$) and their polyethoxylated derivatives; short-chain alkyl or aryl esters ($C_1$-$C_7$) of $C_4$-$C_{12}$ diacids or diols optionally substituted with one or more hydroxyl groups; alkyl or aryl $C_1$-$C_{10}$ esters of glycerol, pentaerythritol, ethylene glycol, propylene glycol, as well as polyethoxylated derivatives of these and polyethylene glycol; $C_{12}$-$C_{22}$ alkyl esters or ethers of polypropylene; $C_{12}$-$C_{22}$ alkyl esters or ethers of polypropylene/polyethylene glycol copolymer.

Non-limiting examples of occlusive moisturizing agents include cyclic and linear dimethicones; polydialkylsiloxanes; polyarylalkylsiloxanes; long chain ($C_8$-$C_{36}$)alkyl and alkenyl esters of long straight or branched chain alkyl or alkenyl alcohols or acids; long chain ($C_8$-$C_{36}$)alkyl and alkenyl amides of long straight or branched chain ($C_8$-$C_{36}$) alkyl or alkenyl amines or acids; hydrocarbons including straight and branched chain alkanes and alkenes such as squalene, squalane and mineral oil; jojoba oil; polysiloxane polyalkylene copolymers; short chain alkyl or aryl esters ($C_1$-$C_{36}$) of $C_{12}$-$C_{22}$ diacids or diols optionally substituted with one or more hydroxyl groups such as diisopropyl dimer dilinoleate; and $C_{12}$-$C_{22}$ alkyl and alkenyl alcohols; long chain alkyl or aryl esters ($C_8$-$C_{36}$) of $C_{12}$-$C_{22}$ diacids or diols optionally substituted in available positions by —OH, such as diisostearyl dimer dilinoleate; lanolin and lanolin derivatives; and beeswax and its derivatives.

Non-limiting examples of humectant-type moisturizing agents include glycerol, polyglycerols (including: diglycerol, triglycerol, polyglycerin-3, tetraglycerol, hexaglycerol, decaglycerols), propylene glycol, dipropylene glycol, polypropylene glycol, polyethylene glycol (PEG-2 to PEG-45M; e.g., a molecular weight between about 300 and 1,000), sorbitol, polyhydric alcohol ethoxylates (e.g., sorbeth-6, sorbeth-30, glycereth-1 to glycereth-31), methoxides of polyethylene glycol (Methoxy PEG-2 to Methoxy PEG-100), methoxides of polyhydric alcohol ethoxylates (e.g., glycereth-7 methoxide), pantothenol, gluconic acid salts and the like. Other humectant-type agents like that could also be employed include: 1,2,6-hexanetriol, acetamide mea, aluminum hydroxide, arginine pea, butoxypropanol, butylene glycol, dimethyl imidazolidinone, dimethylsilanol hyaluronate, dipotassium glycyrrhizate, erythritol, ethoxy-diglycol, fructose, glucamine, gluconic acid, glucose, glucose glutamate, glucuronic acid, glutamic acid, glycogen, glycyrrhizic acid, heilmoor clay, hexacosyl glycol, histidine, hyaluronic acid, hydrogenated honey, hydrogenated starch, hydrolysate, hydrolyzed collagen, hydrolyzed elastin, hydrolyzed glycosaminoglycans, hydrolyzed keratin, hydrolyzed silk, hydrolyzed soy protein, hydrolyzed wheat protein, hydroxyethyl sorbitol, inositol, inositol hexa-pea, lactamide mea, lactic acid, lactitol, lactose, lysine pea, magnesium pea, maltitol, manganese pea, mannitol, mel (honey extract), menthyl pea, methyl gluceth-10, methyl gluceth-20, pea (pidolic acid), lactamide, polydextrose, polyglucuronic acid, polyglyceryl sorbitol, potassium pea, ppg-20 methyl glucose ether, ppg-38-buteth-37, saccharide isomerate, serica, silk amino acids, sodium carboxymethyl chitin, sodium lactate, sodium mannuronate methylsilanol, sodium pea, sodium pea methylsilanol, sodium polyglutamate, soluble collagen, sorbitol, sucrose, tea-lactate, tea-pea, trehalose, trilactin, urea, xylitol, *Zea mays*, zinc pea, and combinations thereof.

The addition of one or more moisturizing agents may affect the viscosity and stability of the compositions of the present invention. In some embodiments, a single moisturizing agent may be added to the composition. In some embodiments, two or more moisturizing agents may be added to the composition. While any of a variety of moisturizing agents may be added to the formulations of the present invention, some embodiments will include wax and oil type moisturizing agents either alone or combined with water soluble moisturizing agents. In some embodiments of the invention, moisturizing agent systems can be comprised of humectants in addition to occlusive wax and oil moisturizing agents in concentrations that achieve a moisturizing effect and which maintains and improves the condition of the skin upon repeated use. Moisturizing agents may be non-comedogenic and chosen to avoid skin irritation or sensitization reactions.

D. Thickening Agent

In some embodiments, the compositions of the present invention include a thickening agent.

In some embodiments, the thickening agent is a polyvinyl carboxy polymer (or carbomer), such as carbopol 940. Other thickening agents include gums such acacia, alginic acid or a salt thereof (e.g., sodium alginate), tragacanth, and xanthan gum bentonite, carboxymethyl cellulose, ethylcellulose, gelatin, hydroxyethyl cellulose, hydroxypropyl cellulose, magnesium aluminum silicate methylcellulose, poloxamers, and polyvinyl alcohol.

E. pH-Adjusting Agent

In some embodiments, the compositions of the present invention comprise a pH-adjusting agent.

In one aspect, the pH-adjusting agent is a base. Suitable pH-adjusting bases include bicarbonates, carbonates, hydroxides (e.g., ammonium hydroxide, alkali or alkaline earth metal hydroxides, transition metal hydroxides), and the like. In an alternative aspect, suitable pH-adjusting bases include amines, such as diethanolamine, triethanolamine, or aminopropanol. Additionally or alternatively, the pH-adjusting agent can be an acid, an acid salt, or mixtures thereof. In an embodiment, the pH-adjusting agent comprises two agents (e.g., sodium hydroxide and hydrochloric acid) that are included as needed to adjust the final pH of the composition to a desired pH.

In an embodiment, the pH-adjusting agent is sodium carbonate. In an further embodiment, the composition comprises about 0.1% to about 5%, about 0.15% to about 4%, about 0.25% to about 3.0%, about 0.5% to about 2.0% or about 1.0% of a pH adjusting agent, such as sodium carbonate.

Other pH-adjusting agents can also be included in the composition, such as other acids, acid salts, or mixtures thereof. Further, the pH-adjusting agent can additionally or alternatively be a buffer. Suitable buffers include citrate/citric acid buffers, acetate/acetic acid buffers, phosphate/phosphoric acid buffers, formate/formic acid buffers, propionate/propionic acid buffers, lactate/lactic acid buffers, carbonate/carbonic acid buffers, and the like.

In some embodiments, the inventive formulation includes a buffer and a second pH-adjusting agent (e.g., sodium hydroxide or hydrochloric acid) to adjust the pH of the composition to a desired pH. In some embodiments, the second pH-adjusting agent comprises two agents (e.g., sodium hydroxide and hydrochloric acid) that are included as needed to adjust the pH of the hydroalcoholic chassis or final composition to a desired pH.

In some embodiments, the formulation is acidic. In some embodiments, the formulation has a pH of below about 7.5, 6.5, 5.5, 4.5, 3.5, or 2.5. In certain other aspects, the pH of the formulation may range from about 1.5 to 7, about 2 to 7, about 3 to 7, about 4 to 7, or about 5 to 7. In still other aspects, the pH of the formulation may range from about 1.5 to 5.5, about 2.5 to 5.5, about 3.5 to 5.5, or about 4.5 to 5.5. The formulation may include a buffering agent to maintain its acidic pH. In some embodiments, the formulation has a pH value between about 4 and 7.

In some embodiments, the formulation is basic. In some embodiments, the formulation has a pH of above about 7, 8, 9, 10, 11, or 12. In certain other aspects, the pH of the formulation may range from about 7 to 12.5, about 7 to 11.5, about 7 to 10.5, about 7 to 9.5, or about 7 to 8.5. In still other aspects, the pH of the formulation may range from about 9 to 12.5, about 9 to 11.5, about 9 to 10.5, or about 8.5 to 10. The formulation may include a buffering agent to maintain its basic pH. In some embodiments, the formulation has a pH value between about 7 and 10.

In some embodiments, the formulation is neutral. In some embodiments, the formulation has a pH of about 7. In certain other aspects, the formulation has a pH from about 6.0 to about 8.5, from about 5.5 to 8.0, about 5.0 to 7.0, about 6.0 to 8.0, about 6.5 to 8.5, or from about 6.5 to 7.5. The formulation may include a buffering agent to maintain its neutral pH. In some embodiments, the formulation has a pH value between about 6.0 and 8.5. In some embodiments, the formulation has a pH value between about 5.0 and 7.0.

F. Preservatives

In some embodiments, the compositions of the present invention include a preservative.

In some embodiments, the preservative is an antioxidant (e.g., vitamin C, vitamin E, butylated hydroxyanisole (BHA), or butylated hydroxytoluene (BHT)). Other preservatives include benzoic acid or a pharmaceutically acceptable salt (e.g., sodium or potassium), citric acid or a pharmaceutically acceptable salt (e.g., sodium or potassium), and etheylenediamine tetraacettic acid (EDTA) or a pharmaceutically acceptable salt (e.g., sodium or potassium).

G. Formulation

In some embodiments, the herbal composition is a cream, a gel, an emulgel, a lotion, an oil, an ointment, a compress, or a poultice. In some embodiments, the herbal composition is a lotion.

In some embodiments, the herbal composition is a cream. In some embodiments, the cream comprises stearic acid, glyceryl stearate, lanolin, liquid paraffin, propylene glycol, sodium borate, water, carbomer, triethanolamine, methylparaben, and propylparaben.

In some embodiments, the herbal composition is a gel. In some embodiments, the gel comprises propylene glycol, ethanol, water, carbomer, triethanolamine, sodium methylparaben, and sodium propylparaben.

Pharmaceutical formulations of the present invention can be prepared by the methods discussed herein and by other methods commonly known by the skilled artisan, such as those discussed in *Manual de Uso de Hierbas Medicinales del Paraguay*, UNESCO, 2001 (e.g., Pt. 3) or *Remington: The Science and the Practice of Pharmacy*, 21st ed.).

In some embodiments, the ratio of the first plant matter to the second plant matter is from about 90:10 to 30:70. In some embodiments, the ratio of the first plant matter to the second plant matter is from about 70:30 to 50:50.

In some embodiments, the ratio between the first and second plant matter or preparation thereof is about 50:50 (e.g., 45:55, 46:54, 47:53, 48:52, 49:51, 50:50, 51:49, 52:48, 53:47, 54:46, or 55:45). In some embodiments, the ratio between the first and second plant matter or preparation thereof is about 60:40. (e.g., about 54:46, 55:45, 56:44, 57:43, 58:42, 59:41, 60:40, 61:39, 62:38, 63:37, 64:36, 65:35, or 66:34). In some embodiments, the ratio between the first and second plant matter or preparation thereof is about 70:30. (e.g., about 77:23, 76:24, 75:25, 74:26, 73:27, 72:28, 71:29, 70:30, 69:31, 68:32, 67:33, 66:34, 65:35, 64:36, or 63:37). In some embodiments, the ratio between the first and second plant matter or preparation thereof is about 80:20. (e.g., about 88:12, 87:13, 86:14, 85:15, 84:16, 83:17, 82:18, 81:19, 80:20, 79:21, 78:22, 77:23, 76:24, 75:25, 74:26, 73:27, or 72:28).

H. Surfactants

In one aspect, the composition may include one or more additional nonionic, cationic, anionic, and/or zwitterionic surfactants. The one or more surfactants may be present at about 0.1% or 0.15% to 10% w/w, such as about 0.1, 0.15, 0.2, 0.3, 0.4, 0.5, 1.0, 1.5, 2, 3, 4, 5, 6, 7, 8, 9 or 10% w/w.

1. Nonionic Surfactants

Non-limiting examples of nonionic surfactants include polysorbates, such as polysorbate 20 (Tween 20), Tween 40, Tween 60, and Tween 80; poly(oxyethylene) (POE) fatty acid esters, such as Myrj 45, Myrj 49, Myrj 52 and Myrj 59; sucrose esters; partial esters of sorbitol and its anhydrides, such as sorbitan monolaurate; mono or diglycerides; and isoceteth-20.

Other non-limiting examples include members of the class of alkyl ester nonionic surfactants with 8 to 100 alkylene glycol repeat units in their polyalkylene glycol polymeric chains (e.g., 8, 40, 50, or 100). In some embodiments, the ester group is derived from a fatty acid. In some embodiments, the polyalkenene glycol is polyethylene glycol.

Other nonionic surfactants include, but are not limited to, cetomacrogol 1000, cetostearyl alcohol, cetyl alcohol, cocoamide diethanolamine, cocoamide monoethanolamine, decyl glucoside, glyceryl laurate, lauryl glucoside, polyoxyethylene ethers of fatty acids such as cetyl alcohol or stearyl alcohol, narrow-range ethoxylates, octyl glucoside, oleyl alcohol, poloxamers, polyethylene glycol, sorbitan monolaurate, polyoxyethylene sorbitan monolaurate, sorbitan dioleate, sorbitan trilaurate, sorbitan monopalmitate, polyoxyethylene (20) sorbitan monopalmitate, sorbitan monostearate, sorbitan tristearate, polyoxyethylene (20) sorbitan monostearate, sorbitan monooleate, sorbitan trioleate, polyoxyethylene sorbitan monooleate, stearyl alcohol, sucrose coconut fatty ester mixtures, glycerin monolaurate, and sucrose monolaurate.

Still other non-ionic surfactants include, but are not limited to, fatty acid diesters, polyethylene glycol glycerol fatty acid esters, alcohol-oil transesterification products, polyglycerized fatty acids, sterol and sterol derivatives, polyethylene glycol alkyl ethers, sugar esters, polyethylene glycol alkyl phenols, polyoxyethylene-polyoxypropylene block copolymers, sorbitan fatty acid esters and lower alcohol fatty acid esters.

In some embodiments, the composition includes at least one pharmaceutically acceptable surfactant that is a polyalkylene glycol alkyl ether. The polyalkylene glycol alkyl ether may be present at up to about 5% w/w, such as about 0.1, 0.15, 0.2, 0.3, 0.4, 0.5, 1.0, 1.5, 2, 2.5, 3, 3.5, 4, 4.5 or 5% w/w. In some embodiments, the polyalkylene glycol alkyl ether is present at up to about 3% w/w, such as about 0.1, 0.15, 0.2, 0.3, 0.4, 0.5, 1.0, 1.25, 1.5, 1.75, 2.0, 2.25, 2.5, 2.75 or 3% w/w.

In some embodiments, the composition includes a polyalkyene glycol alkyl ether; e.g., a polyalkylene glycol alkyl ether such as a polypropylene oxide alkyl ether or a polyethylene glycol alkyl ether. Some non-limiting examples of polyalkylene glycol alkyl ethers include poly(oxyethylene) cetyl ether, poly(oxyethylene) palmityl ether, polyethylene oxide hexadecyl ether, polyethylene glycol cetyl ether, Brij 30, Brij 38, Brij 52, Brij 56, Brij 58, Brij 78, Brij 98, Brij 700, Brij 700P, Brij 721, and Brij W1.

Other non-limiting examples include members of the class of alkyl ether nonionic surfactants with two to 100 alkylene glycol repeat units in their polyalkylene glycol polymeric chains. In some embodiments, the alkyl group is derived from a fatty acid alcohol.

In some embodiments, the polyalkenene glycol is polyethylene glycol.

2. Cationic Surfactants

Non-limiting examples of cationic surfactants include octyl trimethylammonium salts, cetyl trimethyl ammonium salts, stearyl trimethyl ammonium salts, benzyl trimethyl ammonium salts, alkylamines, alkylimidazoles, ethoxylated amines, non-amphoteric quaternary surfactants, esterquats, and a mixture thereof. Quaternary surfactants contain at least one nitrogen atom, which is covalently bonded to four alkyl or aryl groups.

Cationic surfactants include, but are not limited to, non-amphoteric quaternary ammonium compounds, in particular benzyltrialkyl ammonium chlorides or bromides, e.g., benzyl dimethylstearyl ammonium chloride; alkyl trialkyl ammonium salts, e.g., cetyl trimethyl ammonium chloride or bromide, alkyl dimethylhydroxyethyl ammonium chloride or bromide, dialkyl dimethyl ammonium chloride or bromide, and alkylamide ethyltrimethyl ammonium ether sulfates; alkylpyridinium salts, e.g., lauryl or cetyl pyrimidinium chloride; N,N'-dialkylimidazoline derivatives; compounds having cationic character, such as amine oxides, e.g., alkyl dimethylamine oxides or alkylaminoethyl dimethylamine oxides; and the like.

3. Anionic Surfactants

Non-limiting examples of anionic surfactants include alkyl sulfates, e.g., sodium, ammonium or triethylammonium (TEA) lauryl sulfate or laureth sulfate; acylamino acids (and their salts), such as acyl glutamates, e.g., sodium acyl glutamate, di-TEA palmitoyl aspartate, and sodium caprylic/capric glutamate; acyl peptides, e.g., palmitoyl-hydrolyzed milk protein, sodium cocoyl-hydrolyzed soya protein and sodium/potassium cocoyl-hydrolyzed collagen; sarcosinates, e.g., myristoyl sarcosin, TEA-lauroyl sarcosinate, sodium lauroyl sarcosinate and sodium cocoyl sarcosinate; taurates, e.g., sodium lauroyl taurate and sodium methylcocoyl taurate; acyl lactylates, lauroyl lactylate, caproyl lactylate; and alaninates; and the like.

Other anionic surfactants include carboxylic acids and derivatives, such as carboxylic acids, e.g., lauric acid, aluminum stearate, magnesium alkanolate, and zinc undecylenate; ester carboxylic acids, e.g., calcium and sodium stearoyl lactylates, laureth-6 citrate, and sodium PEG-4 lauramide carboxylate; ether carboxylic acids, e.g., sodium laureth-13 carboxylate, and sodium PEG-6 cocoamide carboxylate; and the like.

Other anionic surfactants include esters of phosphoric acid and salts, e.g., dilaureth-4 phosphate.

Other anionic surfactants include sulfonic acids and salts, such as acyl isethionate, e.g., sodium-ammoniumcocoyl isethionate, alkylaryl sulfonates; alkyl sulfonates, e.g., sodium coco monoglyceride sulfate, sodium $C_{12-14}$ olefin-sulfonate, sodium lauryl sulfoacetate and magnesium PEG-3 cocamide sulfate; sulfosuccinates, e.g., dioctyl sodium sulfosuccinate, disodium laureth sulfosuccinate, disodium lauryl sulfosuccinate, disodium undecylenamido-MEA-sulfosuccinate, and PEG-5 lauryl citrate sulfosuccinate; esters of sulfuric acid, such as alkyl ether sulfate, e.g., sodium, ammonium, magnesium, MIPA, TIPA, laureth sulfate, lauryl sulfate, sodium myreth sulfate and sodium $C_{12-13}$ pareth sulfate; and the like.

4. Zwitterionic Surfactants

In one aspect, the composition comprises a zwitterionic surfactant or a charged derivative thereof. In one aspect, the zwitterionic surfactant or charged derivative thereof is selected from the group of disodium cocoamphodiacetate, sodium cocoamphodiacetate, cocoamidopropyl betaine, and a mixture thereof.

Other zwitterionic surfactants or charged derivatives thereof include, but are not limited to, amino acids such as β-N-alkylaminopropionic acids, aminopropyl alkylglutamide, alkylaminopropionic acid, sodium alkylimidodipropionate, dihydroxyethyl alkyl glycinate, and lauroamphocarboxyglycinate; imino acids such as N-alkyl-β-iminodipropionic acids; imidazoline derivatives that are not N,N'-dialkylated; quaternary ammonium amino acid sulfobetaines such as alkyl amidopropyl hydroxysultaines, cocoamidopropyl hydroxysultaine, sodium cocoamphohydroxypropyl sulfonate, or sodium capryloamphohydroxypropyl sulfonate; quaternary ammonium amino acid betaines, e.g., dodecyl betaine; alkyl amidopropyl betaines such as cocoamidopropyl betaine; alkyl dimethyl betaines; phospholipids such as lecithin; acyl dialkyl ethylenediamines, e.g., sodium acyl amphoacetate, disodium acyl amphodipropionate, disodium alkyl amphodiacetate, sodium acyl amphohydroxypropyl sulfonate, disodium acyl amphodiacetate, and sodium acyl amphopropionate; a salt of cocamphodiactetate, such as sodium cocamphodiacetate; and the like.

I. Lower Alcohols and Diols

In some embodiments, the compositions and formulations include a lower alcohol. In some embodiments, the lower alcohol is a monohydric lower alcohol, e.g., a $C_1$ to $C_6$ alkanol, such as methanol, ethanol, propanol, isopropanol, butanol, isobutanol, sec-butanol, pentanol, and the like, or a mixture thereof.

In some embodiments the composition includes about 0% to 60% (w/w) or about 1 to 50% (w/w) of the lower alcohol (e.g., ethanol). In other aspects, the formulations include about 5, 10, 15, 20, 22, 23, 25, 30 32, 33, 35, 36, 40, 41, 42, 45, 50, 55, or 60% (w/w) of a lower alcohol. In some embodiments, the composition comprises from about 5% to 25% (w/w) of a lower alcohol, such as about 5, 6, 7, 8, 9, 10, 11, 11.2, 12, 13, 15, 18, 20, 22, 23, or 25%. Alternatively, the composition comprises from about 1 to 5%, about 1 to 12%, about 5 to 15%, about 5 to 22.5%, about 10 to 23%, about 15 to 30%, about 20 to 40%, about 25 to 50%, about 35 to 50%, about 35 to 60% (w/w) of a lower alcohol. Alternatively, the composition comprises about 22, 22.5, 23, 25, 30, 32, 32.5, 33, 35, 35.5, 36, 39, 39.5, 40, 41, 41.7, 42, or 50% (w/w) of a lower alcohol.

In some embodiments, the formulations include a diol. Suitable diols include, but are not limited to, propylene glycol, butanediol, butynediol, pentanediol, hexanediol, octanediol, neopentyl glycol, 2-methyl-1,3-propanediol, diethylene glycol, triethylene glycol, tetraethylene glycol, dipropylene glycol, dibutylene glycol, propylene glycol, and the like, as well as a mixture thereof. In one aspect, the formulation comprises about 0% to 15% (w/w) of propylene glycol, e.g., about 0 to 8%. In some embodiments, the diol is a glycol, such as ethylene glycol, propylene glycol, or a mixture thereof. In some embodiments, the diol is propylene glycol.

J. Water

In some embodiments, the compositions include water. In some embodiments, water is present from about 5% to 75% (w/w) such as about 5, 6, 7, 8, 9, 10, 11, 12, 12.5, 13, 14, 15, 16, 16.6, 17, 17.5, 18, 18.5, 19, 20, 21, 22, 23, 24, 25, 30, 35, 40, 45, 50, 55, 60, 65, 70 or 75% by weight. In some embodiments, water is present from about 5% to 25% (w/w). In some embodiments, the composition includes from about 5 to 10%, about 10 to 20%, about 10 to 15%, about 15 to 20%, about 20 to 30%, about 30 to 40%, about 40 to 50%, about 50 to 60%, about 60 to 70%, or about 70 to 75% (w/w) water. Alternatively, the mixture includes about 8, 9, 10, 12, 12.5, 13, 16, 16.6, or 17% (w/w) or q.s. water.

II. Methods of Treatment

In some embodiments, the invention sets forth a method for the topical treatment of herpes, wherein the method comprises administering the herbal composition as disclosed in one of the aspects or embodiments disclosed herein to a patient.

In some embodiments, the herpes is herpes type I, II, or III. In some embodiments, the herpes is herpes type I. In some embodiments, the herpes is herpes type II. In some embodiments, the herpes is herpes type I or II. In some embodiments, the herpes is herpes type III.

In some embodiments, the composition is administered topically to a site on the patient's lips. In some embodiments, the composition is administered topically to the patient's skin within about 1" of the lips. In some embodiments, the herpes is herpes type I or II (e.g., type I).

In some embodiments, the composition is administered topically to a site on the patient's genitalia. In some embodiments, the composition is administered topically to patient's skin within about 1" of the genitalia. In some embodiments, the herpes is herpes type I or II (e.g., type II).

In some embodiments, the composition is administered topically to a herpes lesion. In some embodiments, the composition is administered topically to a patient's skin within about 1" of the herpes lesion. In some embodiments, the herpes is type III (e.g., shingles).

In some embodiments, the composition is administered topically to the mucous membrane. In some embodiments, the composition is administered topically to patient's skin within about 1" of the mucous membrane.

In some embodiments, the composition is administered at about 15-min intervals for from about 4 to 10 hours (e.g., 3, 4, 5, 6, 7, 8, 9, 10, or 11 hours).

In some embodiments, the composition is administered at about 4- to 8-hour intervals for about 2 to 7 days (e.g., 1, 2, 3, 4, 5, 6, 7 or 8 days).

In some embodiments, the administering step begins before formation of a blister. In some embodiments, administering may reduce the size of the resulting lesions.

In some embodiments, the method further includes administering an antiviral agent or second treatment agent. In some embodiments, the antiviral agent is acyclovir, valacyclovir, famcyclovir, or penciclovir. In some embodiments, the second treatment agent is lysine, rhubarb and sage, propolis, docosanol, tea tree oil, dimethocmenthol, camphor, benzocaine, or benzoalkonium chloride.

In some embodiments, the subject is a human. Alternatively, the subject is a non-human mammal.

EXAMPLES

Example 1: Formulations

Materials

All ingredients were USP/NF grade materials, and all excipients are available from commercial sources without further custom manufacturing.

Gel Formulation

A gel formulation was prepared by standard procedures at kg scale with the following components:

| | |
|---|---|
| Carbomer 940 (Carbopol 940) | 0.570 kg |
| Propylene glycol | 6 kg |
| Ethanol (96%) | 11 L |
| Distilled water | 34 L |
| Sodium methylparaben | 0.100 kg |
| Sodium propylparaben | 0.043 kg |
| Triethanolamine | 1.02 kg |
| Citric acid | 0.05 kg |
| Plant extracts (liquid from 0.2:1 plant matter: 36% (v/v) ethanol) | 2.5 L |
| Mint green (green coloring) | 0.02 L |

The gel formulation was prepared by a general procedure that is detailed below.

To a stainless steel vessel was added the carbomer 940, followed by the propylene glycol, and 96% alcohol (3 L). The combination was mixed thoroughly.

To a stainless steel marmite was added distilled water (31.0 L). The carbomer mixture was added with continuous stirring, followed by the remaining alcohol (8 L).

A mixture of (i) a tincture prepared from *Jacaranda caucana* and (ii) a tincture prepared from *Spilanthes americana* was prepared with the proportions indicated (e.g., 50:50; 70:30; 80:20).

To the marmite was added the plant extracts (2.5 L of the combined tinctures) and then the mint green color with continuous stirring. The mixture was shaken until homogeneous.

To the marmite was added the triethanolamine.

To a second stainless steel vessel was added the sodium methylparaben, the sodium propylparaben, and the remaining distilled water (2.0 L). The paraben mixture was added to the marmite with mixing to form the gel formulation.

The pH of the gel formulation was measured. If necessary to adjust the pH of the mixture to between 5.0 to 7.0, citric acid was added to the mixture (e.g., 0.05 kg).

Cream Formulation

A cream formulation was prepared by standard procedures at 60 g scale with the following components:

| | |
|---|---|
| Plant extracts (liquid from 0.2:1 plant matter: 36% (v/v) ethanol) | 6 mL |
| Mineral oil | 7.92 g |
| Stearic acid | 3 g |
| Cetyl alcohol | 3.9 g |
| Borax | 0.504 g |
| Methyl paraben | 0.12 g |
| Propyl paraben | 0.06 g |
| Propylene glycol | 6.852 g |
| Triethanolamine | 0.288 g |
| Carboxymethylcellulose, sodium salt | 0.036 g |
| Lanolin | 3.9 g |
| Essence blue crystal (perfume) | 0.42 g |
| Distilled water | 27 mL |

The cream formulation was also prepared by standard procedures at 6 kg scale with the following components:

| | |
|---|---|
| Plant extracts (liquid from 0.2:1 plant matter: 36% (v/v) ethanol) | 600 mL |
| Mineral oil | 792 g |
| Stearic acid | 300 g |
| Cetyl alcohol | 390 g |
| Borax | 50.4 g |
| Methyl paraben | 12 g |
| Propyl paraben | 6 g |
| Propylene glycol | 685.2 g |
| Triethanolamine | 28.8 g |
| Carboxymethylcellulose, sodium salt | 3.6 g |
| Lanolin | 390 g |
| Essence blue crystal (perfume) | 42 g |
| Distilled water | 2.700 L |

Essence blue crystal is a perfuming agent that provides the finished cream with a pleasant odor. It is not an active ingredient.

The cream formulation was prepared by a general procedure that is detailed below.

Distilled water was heated at 70° C.±5° C. in a stainless steel receptacle.

In a separate, stainless steel container, the oily, organic formulation components (e.g., the stearic acid, cetyl alcohol, lanolin) were heated with the mineral oil and parabens, without exceeding 70° C.±5° C. (i.e., at or below 75° C.).

In still another container, the carboxymethylcellulose component was dispersed in propylene glycol, at room temperature.

To a stainless steel marmite provided with a shirt and stirrer for creams was added the hot water. As the mixture was stirred, the propylene glycol/carboxymethylcellulose dispersion was added, followed by the borax and triethanolamine. The already melted oil phase was then added to the aqueous mixture as it was continuously stirred.

A mixture of (i) a tincture prepared from *Jacaranda caucana* and (ii) a tincture prepared from *Spilanthes americana* was prepared with the proportions indicated (e.g., 70:30).

Cold water was added to the outside of the marmites to allow the emulsion to cool down. Stirring was suspended for 15 minutes and then restarted for two minutes periods at 10-minute intervals. When the mixture has reached 30° C., the plant tincture mixture was added, and the mixture was stirred for 5 min.

The resulting cream was allowed to cool to room temperature (about 17-20° C.) without further agitation.

Example 2

A gel that included a 1:1 of the first (*Jacaranda*) and second (*Spilanthes*) plant materials as extracts was prepared according to the formula of Example 1. The gel was used for the treatment of cold sores in an adult woman. Upon the patient's perception of a burning sensation around her mouth, which corresponded to the appearance of the typical papule of the herpes virus infection, she applied the medication to the lesion site. She reported immediate relief from the symptoms and complete disappearance of the burning sensation within 2 hours. She reported that the burning sensation began again after about 2 hours. A second application of the gel was made 8 hours after the first application and repeated every 8 hours. After 3 days of gel application, the treatment continued to provide relief, and the lesion had healed to a scab. However, the scab was smaller than those from prior, untreated lesions. After 6 days of gel application, the scab had completely healed, while untreated lesions typically required 12 to 15 days for complete healing.

Example 3

A 30-year-old woman with cold sores had a history of unresponsiveness to oral and topical acyclovir, which instead produced side effects like dizziness. She was treated with a gel that included a 70:30 mixture of *Jacaranda* plant matter and *Spilanthes* plant matter, but was otherwise prepared according to Example 1. She reported that upon feeling the symptom of a burning sensation, indicating the formation of a papule, she began to apply the compound. She applied the compound topically every 6 hours and reported that it controlled the symptoms. She still developed a scab, although it was smaller than usual and it healed quicker.

Example 4

A 70-year-old woman developed a papule located between her upper lip and her nose. The papule was accompanied by the typical itching sensation. She began the treatment with the 70:30 gel of Example 3, but she applied the compound every 15 minutes during waking hours for 3 days. The burning sensation was suppressed during the entire period. The swelling stopped, and the papule healed without forming a scab.

Example 5

A 58-year-old man reported that he was unresponsive to known treatments for his cold sores. He was treated with the 1:1 gel of Example 1 and instructed to apply the treatment every 15 minutes, but he only began the application late that afternoon. A itching sensation started that night. He did not use the medicine the next day, and he developed a papule on his lip, which formed a vesicle. At night he continued the treatment, and the burning sensation stopped upon application. He did two applications before going to sleep, and he continued the treatment the next day. Despite the fact that he had already developed a vesicle, the medication relieved his symptoms. He reported that the vesicle stopped growing and the symptoms disappeared. After continued treatment, the vesicle turned into a small scab that healed more quickly than prior scabs.

Example 6

A 10-year-old boy used an 80:20 gel compound on a cold sore that he had developed. He applied the gel every 15 minutes to the location at which a small papule had appeared and at which he also reported feeling a burning sensation. He had to apply the compound every 15 minutes to suppress the burning sensation. The swelling of the papule stopped, but more did so more slowly than for other patients using the 70:30 gel.

Example 7

A 49-year-old man was treated with the 70:30 gel, which he applied every 15 minutes. He began to apply the composition the third day after the onset of the cold sore. The composition immediately stopped the progression of the cold sore. An untreated vesicle typically breaks the skin, leaving an ulcer over which a scab forms. In this case, the man's scab was very small, which is in contrast to other medications that leave a much bigger scab due to their inability to stop the development of the cold sore.

Example 8

A 40-year-old woman presented with a cold sore forming close to her nose. She was treated with a 70:30 gel applied every 15 minutes. The treatment was applied from the beginning of the itch and papule. The pain and discomfort stopped immediately, and the papule healed without forming a scab.

Example 9

A 50-year-old woman presented with a cold sore that had begun forming on her upper lip during the previous night, which she reported as causing an intense burning sensation. She began application of a 70:30 gel that night, which provided immediate relief from the burning sensation. The next day, the treated sore had stopped growing, but three more lesions formed on her right upper lip. Application of the gel to the other lesions stopped their growth as well. Scab formation was quick, and the scabs fell off after one week rather than two weeks.

It is understood that the examples and embodiments described herein are for illustrative purposes only. Various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. An herbal composition, wherein the composition comprises:
   a first plant matter or preparation thereof, wherein the first plant matter is from *Jacaranda* sp., wherein the *Jacaranda* sp. is *Jacaranda caucana* Pittier; and
   a second plant matter or preparation thereof, wherein the second plant matter is from *Spilanthes* sp;
   wherein the herbal composition is a cream, a gel, an emulgel, a lotion, or an ointment.

2. The herbal composition of claim 1, wherein the ratio of the first plant matter to the second plant matter is from about 70:30 to 50:50.

3. The herbal composition of claim 1, wherein the *Spilanthes* sp. is *Spilanthes americana*.

4. The herbal composition of claim 1, wherein the first plant matter or preparation thereof is an extract.

5. The herbal composition of claim 1, wherein the second plant matter or preparation thereof is an extract.

6. The herbal composition of claim 1, wherein the herbal composition is a cream or a gel.

7. The herbal composition of claim 6, wherein the herbal composition further comprises:
   (i) a moisturizing agent;
   (ii) a thickening agent;
   (iii) a pH-adjusting agent; and
   (iv) a preservative.

8. The herbal composition of claim 6, wherein the herbal composition is the cream.

9. The herbal composition of claim 8, wherein the cream comprises stearic acid, glyceryl stearate, lanolin, liquid paraffin, propylene glycol, sodium borate, water, carbomer, triethanolamine, methylparaben, and propylparaben.

10. The herbal composition of claim 6, wherein the herbal composition is the gel.

11. The herbal composition of claim 10, wherein the gel comprises propylene glycol, ethanol, water, carbomer, triethanolamine, sodium methylparaben, and sodium propylparaben.

12. The herbal composition of claim 1, wherein the ratio of the first plant matter to the second plant matter is from about 90:10 to 30:70.

13. The herbal composition of claim 6, wherein the ratio of the first plant matter to the second plant matter is from about 70:30 to 50:50.

14. A method for the topical treatment of herpes, wherein the method comprises administering an herbal composition to a patient;
wherein the herbal composition comprises:
a first plant matter or preparation thereof, wherein the first plant matter is from *Jacaranda* sp., wherein the *Jacaranda* sp. is *Jacaranda caucana* Pittier; and
a second plant matter or preparation thereof, wherein the second plant matter is from *Spilanthes* sp.

15. The method of claim 14, wherein the herpes is herpes type I, II, or III; and wherein the composition is administered topically to a herpes lesion or on the patient's skin within about 1 inch of the herpes lesion.

16. The method of claim 14, wherein the herpes is herpes type I or II, and wherein the composition is administered topically to a site on the patient's mucous membrane or on the patient's skin within about 1 inch of the mucous membrane.

17. The method of claim 14, wherein the herpes is herpes type I or II, and wherein the composition is administered topically to a site on the patient's genitalia or on the patient's skin within about 1 inch of the genitalia.

18. The method of claim 14, wherein the herpes is herpes type III, and wherein the composition is administered topically to a site on the patient's skin.

19. The method of claim 14, wherein the composition is administered at about 15-min intervals for from about 4 to 10 hours.

20. The method of claim 14, wherein the administering step begins before formation of a blister.

* * * * *

UNITED STATES PATENT AND TRADEMARK OFFICE
CERTIFICATE OF CORRECTION

PATENT NO. : 11,191,795 B2
APPLICATION NO. : 16/280724
DATED : December 7, 2021
INVENTOR(S) : Carrasco Nino It is certified that error appears in the above-identified patent and that said Letters Patent is hereby corrected as shown below:

In the Specification

Column 4, Line 4: "Jacaranda caucana, Pittier" should be corrected to "Jacaranda caucana Pittier"

Column 4, Line 45: "0.5.5" should be corrected to "5.5"

Column 5, Line 59: "EP patent application" should be corrected to "EP Patent Publication"

Column 11, Line 46: "30 32" should be corrected to "30, 32"

Column 14, Line 43: "When the mixture has reached" should be corrected to "When the mixture reached"

Column 15, Line 56: "more did so more slowly" should be corrected to "did so more slowly"

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*